United States Patent
Koizumi et al.

(10) Patent No.: US 11,944,261 B2
(45) Date of Patent: Apr. 2, 2024

(54) ELECTRONIC ENDOSCOPE SYSTEM AND DATA PROCESSING DEVICE

(71) Applicant: HOYA CORPORATION, Tokyo (JP)

(72) Inventors: Ryohei Koizumi, Tokyo (JP); Yousuke Ikemoto, Tokyo (JP); Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 692 days.

(21) Appl. No.: 17/251,930

(22) PCT Filed: Sep. 12, 2019

(86) PCT No.: PCT/JP2019/035963
§ 371 (c)(1),
(2) Date: Dec. 14, 2020

(87) PCT Pub. No.: WO2020/066670
PCT Pub. Date: Apr. 2, 2020

(65) Prior Publication Data
US 2021/0321856 A1 Oct. 21, 2021

(30) Foreign Application Priority Data

Sep. 27, 2018 (JP) ................................. 2018-182035

(51) Int. Cl.
*A61B 1/00* (2006.01)
*A61B 1/31* (2006.01)
(Continued)

(52) U.S. Cl.
CPC .... *A61B 1/00006* (2013.01); *A61B 1/000094* (2022.02); *A61B 1/0005* (2013.01);
(Continued)

(58) Field of Classification Search
CPC .......... A61B 1/00006; A61B 1/000094; A61B 1/0005; A61B 1/00097; A61B 1/31;
(Continued)

(56) References Cited

U.S. PATENT DOCUMENTS

| 2005/0261550 A1* | 11/2005 | Akimoto | A61B 1/00009 600/101 |
| 2007/0093688 A1* | 4/2007 | Enomoto | A61B 1/00009 600/101 |

(Continued)

FOREIGN PATENT DOCUMENTS

| CN | 101116608 | 2/2008 |
| JP | 2008-061704 A | 3/2008 |

(Continued)

OTHER PUBLICATIONS

Nov. 9, 2021 Japanese Office Action for the corresponding Japanese Patent Application No. 2020-548444.

(Continued)

*Primary Examiner* — Santiago Garcia
(74) *Attorney, Agent, or Firm* — GREENBLUM & BERNSTEIN, P.L.C.

(57) ABSTRACT

An electronic endoscope system includes an electronic endoscope, a processor that includes an evaluation unit, and a monitor. The evaluation unit includes an image evaluation value calculation unit that calculates an image evaluation value indicating an intensity of lesion in the living tissue for each of a plurality of images of the living tissue, and a lesion evaluation unit that calculates a representative evaluation value of the image evaluation value from the image evaluation values of the plurality of images corresponding to a plurality of sections for each of the plurality of sections in which a region of the organ is divided using information of an imaging position in the organ whose image is captured (Continued)

and evaluates an extent of the lesion in a depth direction inside the organ using the representative evaluation value.

8 Claims, 10 Drawing Sheets

(51) Int. Cl.
 *G06T 7/11* (2017.01)
 *G06T 7/60* (2017.01)
(52) U.S. Cl.
 CPC ............ *A61B 1/00097* (2022.02); *G06T 7/11* (2017.01); *G06T 7/60* (2013.01); *A61B 1/31* (2013.01); *G06T 2207/10068* (2013.01)
(58) Field of Classification Search
 CPC ... A61B 1/00045; A61B 1/00055; A61B 1/05; A61B 1/0669; A61B 1/07; A61B 1/045; G06T 7/11; G06T 7/60; G06T 2207/10068
 See application file for complete search history.

(56) References Cited

U.S. PATENT DOCUMENTS

| | | | | |
|---|---|---|---|---|
| 2009/0299144 | A1* | 12/2009 | Shigemori | A61B 1/00158 600/178 |
| 2011/0095067 | A1* | 4/2011 | Ohdaira | A61B 17/07207 606/49 |
| 2014/0142433 | A1* | 5/2014 | Greenstein | A61B 10/0291 600/476 |
| 2015/0187063 | A1 | 7/2015 | Takahashi | |
| 2016/0262604 | A1* | 9/2016 | Greenstein | A61B 1/303 |
| 2016/0345808 | A1* | 12/2016 | Inomata | A61B 1/05 |
| 2017/0014017 | A1* | 1/2017 | Obara | A61B 1/015 |
| 2017/0049415 | A1* | 2/2017 | Tsuruta | A61B 1/00094 |
| 2017/0323059 | A1* | 11/2017 | Sasaki | A61B 5/00 |
| 2018/0279866 | A1 | 10/2018 | Makino | |
| 2019/0058844 | A1* | 2/2019 | Sato | A61B 1/0655 |
| 2019/0117167 | A1* | 4/2019 | Kamiyama | A61B 1/000096 |
| 2019/0192048 | A1 | 6/2019 | Makino et al. | |
| 2019/0244351 | A1 | 8/2019 | Dolnik et al. | |
| 2021/0227133 | A1* | 7/2021 | Mizoguchi | A61B 1/042 |
| 2022/0211876 | A1* | 7/2022 | Mizoguchi | A61B 5/0071 |

FOREIGN PATENT DOCUMENTS

| | | |
|---|---|---|
| WO | 2014/192512 | 12/2014 |
| WO | 2017/057680 | 4/2017 |
| WO | 2018/002935 | 1/2018 |
| WO | 2018/002935 A1 | 1/2018 |
| WO | 2018/043550 | 3/2018 |

OTHER PUBLICATIONS

Official Communication issued in International Bureau of WIPO Patent Application No. PCT/JP2019/035963, dated Nov. 19, 2019.
Office Action issued by the China National Intellectual Property Administration (CNIPA) in Chinese Patent Application No. 201980040759.3, dated Mar. 31, 2023.

* cited by examiner

ELECTRONIC ENDOSCOPE SYSTEM AND DATA PROCESSING DEVICE

TECHNICAL FIELD

The present invention relates to an electronic endoscope system and a data processing device for evaluating the extent of lesion in a living tissue in an organ.

BACKGROUND ART

Lesion portions in a living tissue have varying levels of severity, from inflammation in which a mucosal layer of the living tissue becomes thin and rough and red, to ulcers that are partially missing from the mucosal layer and its lower layers. For example, the ulcerative part of an ulcerative colitis (UC) lesion includes white moss and purulent mucus to be white, and the inflamed portion shows red with edema and easy bleeding. Such lesion portions can be imaged and observed with an endoscope system.

However, it is necessary to undergo long-term training under the guidance of a skilled person in order for an operator to be able to distinguish between a normal portion and a lesion portion by the difference in color contained in an image of the endoscope. In addition, it is not easy for even a skilled operator to identify a lesion portion from a slight color difference, and careful work is required. Therefore, it is preferable that the endoscope system provides an evaluation result in which the degree of lesion in the lesion portion in the organ is objectively quantified.

On the other hand, there is known an endoscope system that can suppress fluctuations in the evaluation value of the inflamed portion due to the brightness of the image to stably calculate the evaluation value, and suppress the processing load of the calculation of the evaluation value (Patent Literature 1).

CITATION LIST

Patent Literature

Patent Literature 1: WO 2017/057680 A

SUMMARY OF INVENTION

Technical Problem

The above-mentioned endoscope system includes a light source device that irradiates an object with illumination light, an image acquisition unit that captures the reflected light from the object with an image sensor and acquires a color image containing at least three or more color components, and an evaluation unit obtains an evaluation result regarding a target disease of each pixel based on an angle formed by a line segment connecting a predetermined reference point set in a color plane and a pixel correspondence point in a color plane of each pixel of the color image acquired by the image acquisition unit and a reference axis having a correlation with the target disease in the color plane defined by at least two or more color components among at least three or more color components. The reference axis is set so as to pass through the predetermined reference point. The reference axis is at least one of an axis having a correlation with a target disease showing an inflammation degree of a predetermined value or less and an axis having a correlation with a target disease showing an inflammation degree of a predetermined value or more in the color plane.

According to such a configuration, it is possible to suppress the fluctuation of the inflammation evaluation value due to the brightness of the image, perform stable calculation of the inflammation evaluation value, and suppress the processing load of the calculation of the inflammation evaluation value.

However, when the endoscope system evaluates the degree of lesion such as inflammation of a living tissue inside the organ, the evaluation is limited to the part of the living tissue from which the image has been taken. It is not possible to properly evaluate how much the inflammation has spread in the depth direction in the organ and how wide the inflamed area is. The method of treating a lesion portion is often different depending on evaluation of the extent in the depth direction of the inflamed portion.

Therefore, an object of the invention is to provide an electronic endoscope system and a data processing device capable of evaluating the extent of a living tissue in the depth direction when evaluating the degree of lesion such as inflammation of the living tissue in the organ.

Solution to Problem

One aspect of the invention is an electronic endoscope system that evaluates the degree of lesion in a living tissue in an organ. The electronic endoscope system includes
  an electronic endoscope configured to image a living tissue in an organ,
  a processor that includes an evaluation unit configured to process a plurality of captured images of the living tissue to evaluate the degree of lesion in the organ, and
  a monitor configured to display an evaluation result of the degree of lesion in a screen.
The evaluation unit includes
  an image evaluation value calculation unit configured to calculate an image evaluation value indicating an intensity of lesion in each of a plurality of images of the living tissue inside the organ,
  an imaging position information processing unit configured to associate each of the images captured in the organ with information of an imaging position in the organ, and
  a lesion evaluation unit configured to calculate a representative evaluation value of the image evaluation value from the image evaluation values of a plurality of images of the living tissue captured in each of a plurality of sections in which a captured image of a region in the organ is divided using the information of the imaging position so as to evaluate an extent of the lesion which is continuously spreading in a depth direction of the organ.

It is preferable that the lesion evaluation unit uses statistics of a plurality of the image evaluation values corresponding to captured images of the living tissue for each section as the representative evaluation values.

The statistic is preferably a maximum value of the plurality of image evaluation values.

It is preferable that the lesion evaluation unit is configured to evaluate an intensity of lesion, which is an element of the degree of lesion in the organ, using a plurality of ranks for each section, and
  that the lesion evaluation unit is configured to determine one of the plurality of ranks based on the representative evaluation value and evaluate the intensity of lesion for each section.

It is preferable that the monitor is configured to display a graph illustrating a distribution of the lesions in the depth direction, in which a horizontal axis represents position coordinates indicating a position of the section along the depth direction in the organ and a vertical axis represents the representative evaluation value.

It is preferable that the lesion evaluation unit determines presence or absence of a lesion portion in which the lesion continuously spreads in the depth direction of the organ for each section based on the representative evaluation value,
that the evaluation unit includes a lesion position calculation unit which obtains a section where the lesion portion is located among the sections based on information of the imaging position so as to obtain a start position and an end position of a region of the lesion portion,
that the lesion evaluation unit calculates a length of the lesion portion from the start position and the end position of the lesion portion, and
that the monitor displays at least one of the start position, the end position of the lesion portion, and a length of the lesion portion in a screen.

It is preferable that the lesion evaluation unit determines presence or absence of a lesion portion in which the lesion continuously spreads in a depth direction of the organ for each of the section based on the representative evaluation value,
that the evaluation unit includes a lesion position calculation unit which obtains a section where the lesion portion is located among the sections based on information of the imaging position so as to obtain a start position and an end position of the lesion portion, and
that the lesion evaluation unit evaluates the degree of lesion in the organ from a total value of the representative evaluation values corresponding to a section sandwiched between the start position and the end position of the lesion portion among the sections.

Another aspect of the invention is a data processing device with a monitor which evaluates the degree of lesion in the organ from a plurality of images of the living tissue inside the organ. The data processing device includes
an image evaluation value calculation unit configured to calculate an image evaluation value indicating an intensity of lesion in a living tissue in each of a plurality of captured images of the living tissue inside the organ,
an imaging position information processing unit configured to associate each image captured in the organ with information of an imaging position inside the organ,
a lesion evaluation unit configured to calculate a representative evaluation value of the image evaluation value from the image evaluation values of a plurality of images of the living tissue captured in each of a plurality of sections in which a captured image of a region in the organ is divided using the information of the imaging position so as to evaluate an extent of lesion which is continuously spreading in a depth direction of the organ using the representative evaluation value, and
a monitor configured to display an evaluation result of the extent of lesion in a screen.

Advantageous Effects of Invention

According to the above-mentioned electronic endoscope system and the data processing device, when evaluating the degree of lesion of a living tissue in an organ, it is possible to accurately evaluate the extent of the living tissue in the depth direction of the organ.

DESCRIPTION OF EMBODIMENTS

Figure 1:
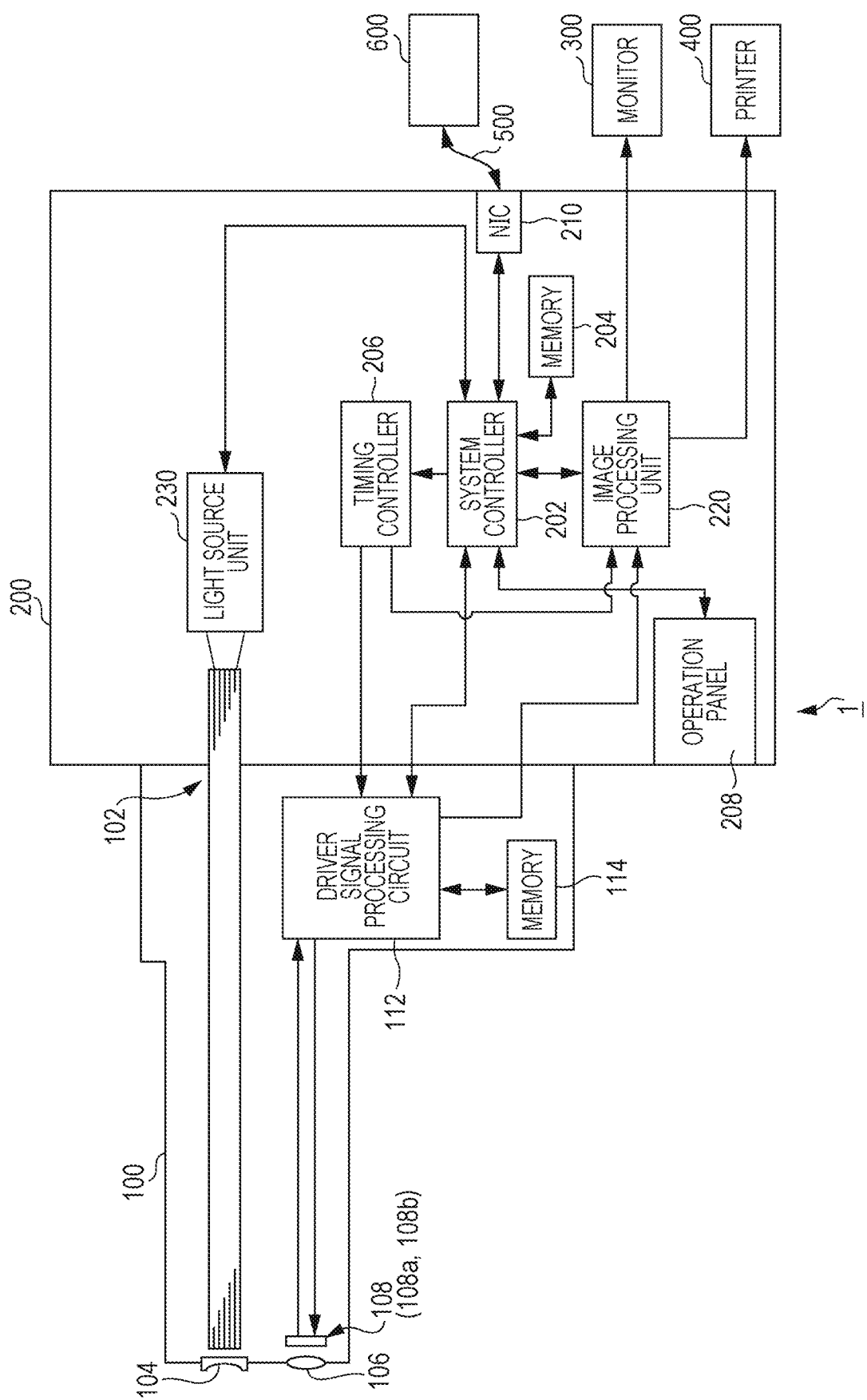
FIG. 1 is a block diagram illustrating a configuration of an endoscope system according to an embodiment.

Hereinafter, before an electronic endoscope system and a data processing device according to an embodiment of the invention are described with reference to the drawings, first, the evaluation of the extent of lesion inside the organ will be conceptually described.
(Outline of Evaluation of the Degree of Lesion Inside an Organ)
A processor of the electronic endoscope system of the embodiment described below processes an image of a living tissue in an organ imaged by an electronic endoscope to evaluate the degree of lesion in the organ. The degree of lesion in an organ includes the extent of lesion and the intensity of lesion, which represents the degree of progression of lesion at each location, as factors in the degree of lesion in the organ. When imaging a living tissue inside an organ, for example, an electronic scope is inserted from the open end of a tubular organ to the deepest position inside the organ to be imaged in the depth direction, and captures the images of the living tissue inside the organ while moving substantially toward the open end of the organ from there. The depth direction includes both an advancing direction from the open end to the deepest side and an advancing direction from the deepest side to the open end side.
The captured images of the living tissue may be moving images continuously captured at certain time intervals, or may be still images captured intermittently while moving the electronic endoscope in the organ. When moving the electronic endoscope, the moving speed of the electronic endoscope does not necessarily have to be constant. The electronic endoscope may capture the images by returning to a place where the electronic endoscope has passed, that is, by making the moving direction partially opposite. In one embodiment, in the case of moving images, the electronic endoscope captures the images while moving in substantially the same direction at substantially the same moving speed.

In the evaluation of the degree of lesion within an organ, the processor calculates, for example, for each of a plurality of images of the living tissue illuminated by a white light, an image evaluation value indicating the intensity of lesion in each image. This image evaluation value is not particularly limited, but may be an inflammation evaluation value for evaluating the lesion, for example, when the lesion is inflammation, based on the information (for example, redness) of the color component of a lesion portion as the intensity of inflammation of the lesion portion (inflamed portion).

The organ to be evaluated is not particularly limited, and examples thereof may include a digestive tract such as pharynx to esophagus, stomach, small intestine, and large intestine.

Further, for example, a living tissue is illuminated and imaged using special light including a laser beam having a wavelength of 405 nm, a laser beam having a wavelength of 445 nm, and fluorescence of 445 to 700 nm obtained by emitting a fluorescent body with a laser beam having a wavelength of 445 nm. Then, the ratio of two image signals is created from the three RGB image signals obtained by imaging, and the evaluation value for each image created by using the processing result of a predetermined highlight processing on these two image signals, for example, an evaluation value for evaluating mucosa or the like in atrophic gastric inflammation, can be used as the image evaluation value.

Further, for example, a living tissue is illuminated with the light having a wavelength of 600 nm, the light having a wavelength of 630 nm, and the light having a wavelength of 540 nm as illumination light and image, and a processing result obtained by performing a predetermined highlight processing on the image obtained by illumination to create an evaluation value for each image, for example, an evaluation value for evaluating the state of blood vessels of the deep mucosa can be used as the image evaluation value.

In addition, the cells of the mucosa of the digestive tract, which are illuminated with light and have been pretreated by staining or the like, are magnified and imaged, and an average value of the feature quantities (shape information of length, diameter, circumference, roundness, etc.) of the cell nuclei can be used as the image evaluation value for evaluating the intensity of lesion such as non-tumor, adenoma, cancer, and the like.

Further, the image evaluation value may be an evaluation level such as a Mayo score obtained for each image. In this case, a representative value of the image evaluation value of the lesion portion, which is obtained from the image of the lesion sample of the lesion portion imaged in advance, the extent information (described later) of the lesion portion, and the evaluation level such as the Mayo score are used as learning data so as to make a predictive model machine-learn the correspondence among the representative value, the extent information of the lesion portion, and the evaluation level. Using this machine-learned predictive model, the evaluation level is predicted from the representative value of the image evaluation value of the lesion portion obtained from the newly captured image of the living tissue in the organ and the extent information (described later) of the lesion portion, and the evaluation level may be used as the image evaluation value. Further, the image evaluation value may be a numerical value of the histopathological evaluation for each image.

Further, when the inside of the organ is imaged, the acquired information of the imaging position in the imaged organ is associated with each of the captured images.

The processor uses the acquired imaging position information to calculate the representative evaluation value of the image evaluation value from the image evaluation values of the plurality of images obtained by imaging the living tissue of each of the plurality of sections, and evaluates the extent of lesion which is continuously spread in the depth direction of the organ using the representative evaluation value for each of the plurality of sections obtained by dividing the region in the imaged organ. Evaluating the extent of lesion includes providing information about to which of the plurality of sections the lesion has spread using graph, numerical values, or text information.

Here, the section is a section divided by a distance equal to or longer than a sampling interval of the imaging position. According to one embodiment, this section is a section divided at predetermined intervals. The predetermined interval may be a constant interval or may not be constant. Further, the predetermined interval may be changed at any time during the calculation of the representative evaluation value. For example, pre-divided sections may be changed to larger sections, for example, segments that are distinguishable from other parts within the organ.

According to one embodiment, the degree of lesion in an organ is evaluated by obtaining a representative value of an image evaluation value corresponding to this section and displaying the distribution of the representative evaluation values in the depth direction for each of the plurality of sections. Alternatively, the evaluation includes providing the total value of the representative evaluation values corresponding to the sections including the lesion portion extracted by using the image evaluation value. Thereby, the degree of lesion in which the extent and the intensity of lesion are evaluated at the same time can be evaluated by dividing it into levels.

The representative evaluation value is a statistic of the image evaluation value for each section, for example, an average value, a median value, a mode value, or a maximum value. Further, when calculating the representative evaluation value while reproducing the image, the representative evaluation value may be the image evaluation value calculated at the end of each section.

In this way, the representative evaluation value of the image evaluation value is calculated from the image evaluation value for each of the plurality of sections, where the captured image of the region inside the organ is divided, using the information of the imaging position in the organ in which each image is captured, so that the extent of lesion can be accurately evaluated. The representative evaluation value is an index of the intensity of lesion in the section. Therefore, it is possible to accurately evaluate not only the local lesion intensity of a living tissue for each of the plurality of captured images, but also the comprehensive evaluation including the lesion extent and the lesion intensity in the depth direction of the organ. Here, the extent of lesion indicates that the lesions are continuously spread in the depth direction. For this reason, it is difficult to evaluate the extent of lesion even if the image is discretely imaged at several positions in the organ to evaluate the image evaluation value.

(Electronic Endoscope System)

FIG. 1 is a block diagram illustrating an example of a configuration of an electronic endoscope system 1 of this embodiment of the invention. As illustrated in FIG. 1, the electronic endoscope system 1 includes an electronic scope 100, an electronic endoscopy processor 200, a monitor 300, and a printer 400.

The electronic endoscopy processor 200 includes a system controller 202 and a timing controller 206. The system controller 202 executes various programs stored in a memory 204 and integrally controls the entire electronic endoscope system 1. Further, the system controller 202 changes various settings of the electronic endoscope system 1 according to an instruction by the user (operator or assistant) input to an operation panel 208. The timing controller 206 outputs a clock pulse for adjusting the operation timing of individual units to individual circuits in the electronic endoscope system 1.

The electronic endoscopy processor 200 includes a light source unit 230 that supplies illumination light to the electronic scope 100. Although not illustrated, the light source unit 230 includes, for example, a high-brightness lamp that emits white illumination light by receiving drive power from a lamp power source, for example, a xenon lamp, a metal halide lamp, a mercury lamp, or a halogen lamp. The light source unit 230 is configured such that the illumination light emitted from the high-brightness lamp is focused by a condensing lens (not illustrated) and then incident on the incident end of an LCB (Light Carrying Bundle) 102 of the electronic scope 100 via a dimmer (not illustrated).

Alternatively, the light source unit 230 includes a plurality of light emitting diodes that emit light in a wavelength band of a predetermined color. The light source unit 230 is configured such that the light emitted from the light emitting diode is synthesized using an optical element such as a dichroic mirror, and the combined light is collected as illumination light by a condensing lens (not illustrated), and then incident on the incident end of the LCB (Light Carrying Bundle) 102 of the electronic scope 100. A laser diode may be used instead of the light emitting diode. The light emitting diode and the laser diode have features such as low power consumption and low heat generation amount as compared with other light sources, and therefore have an advantage that bright images can be acquired while suppressing power consumption and heat generation amount. By acquiring a bright image, it is possible to improve the accuracy of the evaluation value regarding inflammation described later.

In the example illustrated in FIG. 1, the light source unit 230 is built in the electronic endoscopy processor 200, but may be provided in the electronic endoscope system 1 as a device separate from the electronic endoscopy processor 200. Further, the light source unit 230 may be provided at the tip end portion of the electronic scope 100 described later. In this case, the LCB 102 that guides the illumination light is unnecessary.

The illumination light incident on the LCB 102 from the incident end propagates in the LCB 102 and is emitted from the end of the LCB 102 arranged in the tip end portion of the electronic scope 100, and is emitted to the living tissue inside the organ, which is the object, through a light distribution lens 104. The reflected light from the living tissue forms an optical image on the light receiving surface of a solid-state image sensor 108 via an objective lens 106.

The solid-state image sensor 108 is, for example, a single-plate color CCD (Charge-Coupled Device) image sensor in which various filters such as an IR (Infrared) cut filter 108a and a Bayer-arranged color filter 108b are arranged on the light receiving surface, and generates primary color signals of R (Red), G (Green), and B (Blue) according to the optical image formed on the light receiving surface. Instead of the single-plate color CCD image sensor, a single-plate color CMOS (Complementary Metal Oxide Semiconductor) image sensor can also be used. CMOS image sensors generally tend to have an overall darker image than CCD image sensors. Therefore, the advantageous effect of suppressing the fluctuation of the severity of the lesion in the lesion portion due to the brightness of the image is more remarkable than when using the CMOS image sensor in the numerical processing for evaluating the degree of lesion described below. In this way, the electronic scope 100 uses the solid-state image sensor 108 to image the living tissue inside the organ and generate a moving image.

A driver signal processing circuit 112 is provided in a connection portion where the electronic scope 100 is connected to the processor 200. The driver signal processing circuit 112 generates an image signal (brightness signal Y, color difference signals Cb and Cr) by performing predetermined signal processing such as color interpolation and matrix calculation on the primary color signal input from the solid-state image sensor 108, and outputs the generated image signal to an image processing unit 220 of the electronic endoscopy processor 200. The driver signal processing circuit 112 also accesses a memory 114 and reads out device-specific information of the electronic scope 100. The device-specific information of the electronic scope 100 recorded in the memory 114 includes, for example, the number of pixels and sensitivity of the solid-state image sensor 108, an operable frame rate, a model number, or the like. The driver signal processing circuit 112 outputs the device-specific information read from the memory 114 to the system controller 202.

The system controller 202 performs various calculations based on the information stored in the memory 204 and the device-specific information of the electronic scope 100, and generates a control signal. The system controller 202 controls the operation and timing of various circuits in the electronic endoscopy processor 200 using the generated control signal so as to perform processing suitable for the electronic scope 100 connected to the electronic endoscopy processor 200.

The timing controller 206 supplies clock pulses to the driver signal processing circuit 112, the image processing unit 220, and the light source unit 230 in accordance with timing control by the system controller 202. The driver signal processing circuit 112 performs driving control of the solid-state image sensor 108 at a timing synchronized with the frame rate of the video image processed on the electronic endoscopy processor 200 side in accordance with the clock pulses supplied from the timing controller 206.

The image processing unit 220 is a portion capable of performing image processing according to an operator's instruction or according to preset processing contents. Under the control of the system controller 202, the image processing unit 220 generates a video signal for displaying an endoscopic image or the like on a monitor based on the image signal of the captured image input from the driver signal processing circuit 112, and outputs the video signal to the monitor 300. Further, as a part of image processing, the image processing unit 220 processes a plurality of captured images of the living tissue to evaluate the degree of lesion in the organ, and generates a video signal for displaying the evaluation result on a monitor, and outputs the video signal to the monitor 300. Specifically, the image processing unit 220 calculates an image evaluation value described later, which indicates the intensity of lesion of the living tissue in each image, from the plurality of images of the living tissue obtained by the electronic scope 100. The electronic scope 100 images the living tissue inside the organ at a set frame rate while continuously moving along the depth direction of the organ (also including a case where the imaging position in the depth direction is partially displaced in the opposite direction). Therefore, the image processing unit 220 calculates the representative evaluation value of the image evaluation value for each of the plurality of sections obtained by dividing the captured image of the region inside the organ at predetermined intervals using the image evaluation values of the images continuously captured along the substantially depth direction and the information of the imaging position in the organ obtained by imaging each of the plurality of images, and evaluates the extent of lesion which is continuously spreading in the depth direction in the organ using the representative evaluation value.

Further, the image processing unit 220 generates a color map image in which each pixel in the image is given a color according to a pixel evaluation value described later. The image processing unit 220 generates a video signal for displaying the information on the evaluation result of the degree of lesion in the organ and the color map image on the monitor, and outputs the video signal to the monitor 300. This allows the operator to evaluate the degree of lesion spreading in the depth direction of the organ of interest through the image displayed on the display screen of the monitor 300. The image processing unit 220 outputs the color map image and the information on the evaluation result of the degree of lesion in the organ to the printer 400 as needed.

The electronic endoscopy processor 200 is connected to a server 600 via a NIC (Network Interface Card) 210 and a network 500. The electronic endoscopy processor 200 can download information about endoscopic examination (for example, electronic medical record information of a patient, information of an operator, evaluation result of the degree of lesion in the same organ in the past) from the server 600. The downloaded information is displayed, for example, on the display screen of the monitor 300 or the operation panel 208. In addition, the electronic endoscopy processor 200 uploads the endoscopic examination results (endoscopic image data, examination conditions, evaluation results of the degree of lesion of an organ, operator's view, etc.) to the server 600 so as to store the results in the server 600.

Figure 2:
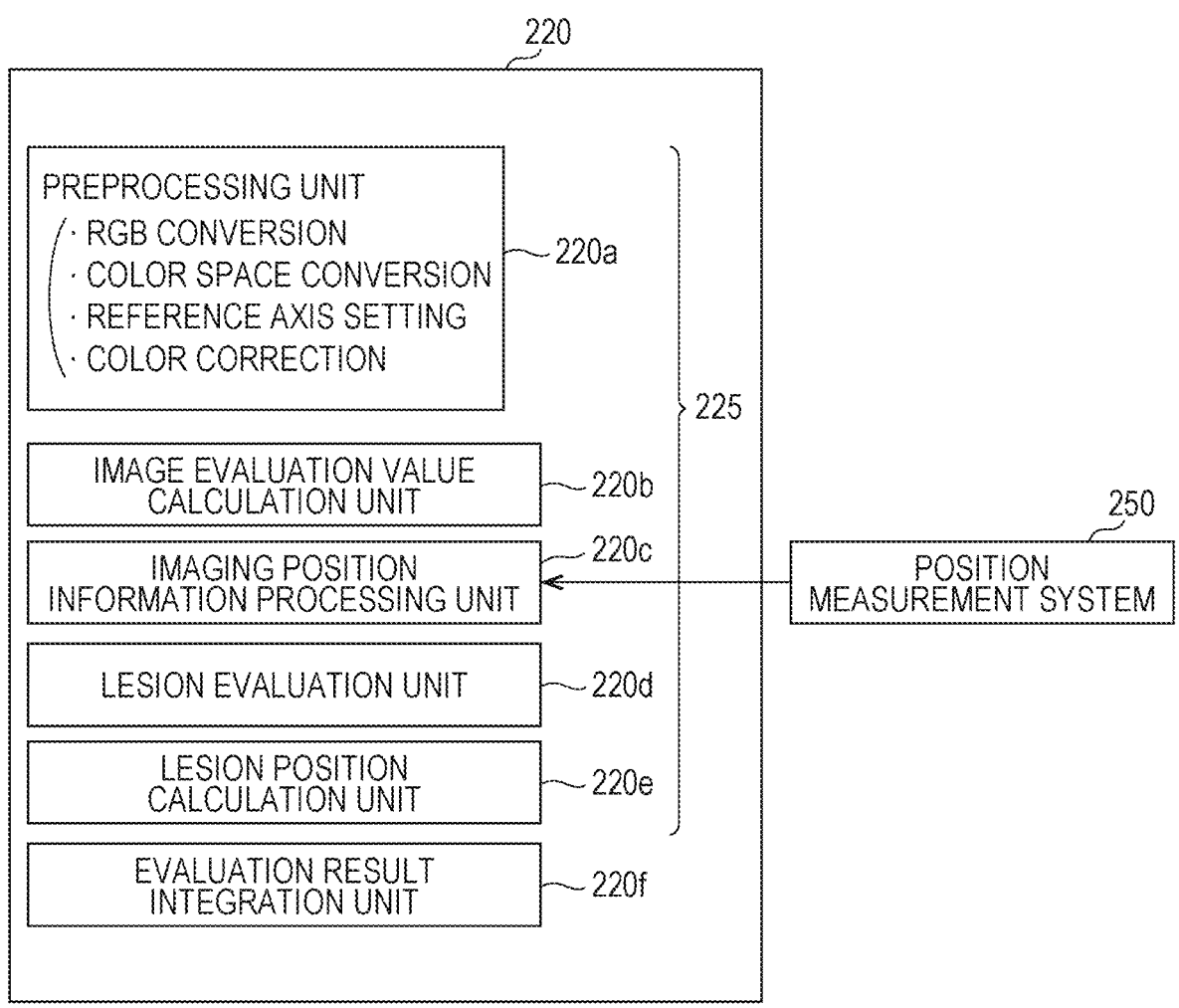
FIG. 2 is a diagram for explaining a configuration of a portion of the image processing unit illustrated in FIG. 1 for evaluating the extent of lesion in the depth direction of an organ.

FIG. 2 is a diagram for explaining the configuration of a part of the image processing unit 220 that evaluates the extent of lesion in the depth direction of an organ. The image processing unit 220 is a portion configured to process a plurality of images of a living tissue captured by the electronic scope 100 and evaluate the degree of lesion. The image processing unit 220 includes a preprocessing unit 220a, an image evaluation value calculation unit 220b, an imaging position information processing unit 220c, a lesion evaluation unit 220d, a lesion position calculation unit 220e, and an evaluation result integration unit 220f. The preprocessing unit 220a, the image evaluation value calculation unit 220b, the imaging position information processing unit 220c, the lesion evaluation unit 220d, the lesion position calculation unit 220e form an evaluation unit which is configured to process a plurality of captured images of the living tissue so as to evaluate the degree of lesion in the organ. The preprocessing unit 220a, the image evaluation value calculation unit 220b, the imaging position information processing unit 220c, the lesion evaluation unit 220d, the lesion position calculation unit 220e, and the evaluation result integration unit 220f may be a software module to be formed by activating a software program stored in the memory 204, or may be configured in hardware.

In the embodiment illustrated in FIG. 2, the image processing unit 220 includes the lesion position calculation unit 220e, but in another embodiment, the image processing unit 220 does not include the lesion position calculation unit 220e.

According to one embodiment, the image evaluation value calculation unit 220b evaluates the intensity of inflammation, which is an example of the intensity of lesion, for each image. Hereinafter, inflammation generated by ulcerative colitis or the like will be described as an example of a lesion.

The image evaluation value calculation unit 220b uses the living tissue redness, which is obtained by quantifying the degree of redness of the living tissue for each pixel, as the pixel evaluation value, and integrates the pixel evaluation values of the entire image to combine the values into one numerical value so as to calculate an image evaluation value. That is, the intensity of inflammation of the living tissue is evaluated by using the degree of redness of the living tissue. Hereinafter, a form for calculating the living tissue redness, which indicates the intensity of inflammation, will be described as an example.

The preprocessing unit 220a is a portion for preprocessing an image for evaluating the degree of redness exhibited by a living tissue. As illustrated as an example, the preprocessing unit 220a performs processing of RGB conversion, color space conversion, reference axis setting, and color correction.

The preprocessing unit 220a converts the image signal (brightness signal Y, color difference signals Cb and Cr) input from the driver signal processing circuit 112 into image color components (R, G, B) using predetermined matrix coefficients.

The preprocessing unit 220a further performs color space conversion in which the image data converted into the image color component is normally projected onto the RG plane. Specifically, the image color component of each pixel in the RGB color space defined by three RGB primary colors is converted into the image color component of RG. Conceptually, the image color component of each pixel in the RGB color space is plotted in the RG plane according to the pixel values of the R and G components (for example, a section in the RG plane taking the pixel value of the R component=0 to 255 and the pixel value of the G component=0 to 255). Hereinafter, for convenience of explanation, the point of the image color component of each pixel in the RGB color space and the point of the image color component plotted in the RG color space are referred to as a "pixel correspondence point". The RGB image color components of the RGB color space are, for example, color components having wavelengths of 620 to 750 nm, wavelengths of 495 to 570 nm, and wavelengths of 450 to 495 nm, respectively. The color components constitute a color space (including a color plane). Hue and saturation are excluded from the "color components".

Further, the preprocessing unit 220a sets a reference axis in the RG plane necessary for evaluating the living tissue redness.

In the living tissue inside the organ of the patient to be an object, the R component among the image color components is dominant over the other components (G component and B component) due to the influence of the hemoglobin pigment and the like. When the degree of lesion in the lesion portion is low and the lesion portion is an inflamed portion, the stronger the inflammation, the stronger the red (R component) with respect to other colors (G component and B component). However, the color of the captured image in the organ changes depending on the imaging conditions that affect the brightness (for example, a condition under illumination light). Illustratively, a shaded area where the illumination light does not reach is black (achromatic color; for example, the values of the image color components of R, G, and B are zero or close to zero), and an area where the illumination light is strongly hit and reflected regularly is white (achromatic color; for example, when the values of the R, G, and B image color components are 8-bit shade, the values are 255 or close to 255). That is, even when the same inflamed portion where inflammation is occurring is imaged, the pixel value of the inflamed portion increases as the illumination light hits the image strongly. Therefore, depending on the condition under the illumination light, the value of the color component of the image may take a value that does not correlate with the intensity of inflammation.

In general, a healthy portion inside the organ having no inflammation is covered with sufficient mucosa. The mucosa is basically white, but the color is slightly yellowish, and the color (yellow) that appears on the image changes depending on the shading (thickness of the mucosa). Therefore, the shading of the mucosa is also considered to be one of the indexes for evaluating the intensity of inflammation. On the other hand, the inflamed portion inside the organ having inflammation is not sufficiently covered with mucosa. Specifically, as the blood vessels dilate, blood and body fluids leak from the blood vessels, and the mucosa becomes relatively thin, so that the color of blood is easily visible.

Figure 3:
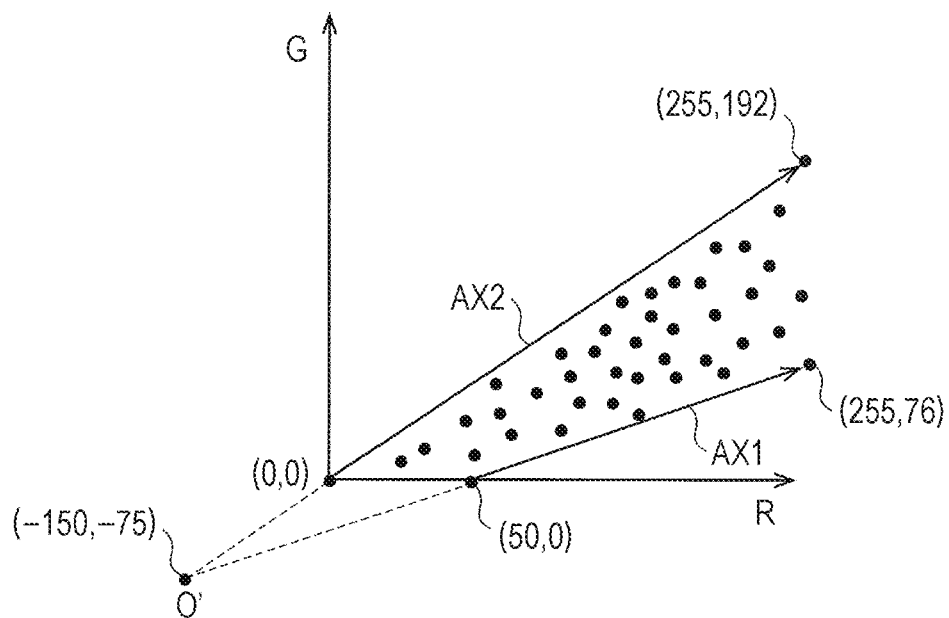
FIG. 3 is a diagram for explaining an example of a reference axis in a color space used in one embodiment.

Therefore, as illustrated in FIG. 3, the straight line passing through (50,0) and (255,76) is set as one of the reference axes in the RG color space, and the straight line passing through (0,0) and (255,192) is set as one of the reference axes. For convenience of explanation, the former reference axis is referred to as "hemoglobin change axis AX1", and the latter reference axis is referred to as "mucosal change axis AX2". FIG. 3 is a diagram for explaining an example of the reference axis in the color space used in one embodiment.

The plot illustrated in FIG. 3 is the result of analyzing a large number of reference images inside the organ. The reference images used for the analysis include the example of inflammatory image of each stage such as an example of an inflammatory image with the highest degree of inflammation (an example of an inflammatory image with the most severe level) and an example of an inflammatory image with the lowest degree of inflammation (an example of an image substantially considered to be a healthy portion). In the example illustrated in FIG. 3, only a part of the plot obtained as a result of the analysis is illustrated for the sake of clarifying the drawing. The actual number of plots obtained as a result of the analysis is much larger than the number of plots illustrated in FIG. 3.

As described above, the stronger the inflammation, the stronger the R component of the color components of the image is with respect to the other components (G component and B component). Therefore, the boundary line between the area where the plots are distributed and the area where the plots are not distributed, which is the axis on the boundary line closer to the R axis than the G axis, that is, the axis on the boundary line passing through (50,0) and (255,76) in the example illustrated in FIG. 3 is set as an axis having a high correlation with the portion having a highest degree of inflammation which is the portion having the highest degree of inflammation. This axis is the hemoglobin change axis AX1. On the hemoglobin change axis AX1, plots corresponding to the inflamed portion having the highest degree of inflammation imaged under various imaging conditions, for example, a condition under the illumination light, are superimposed. Therefore, the hemoglobin change axis AX1 is the axis on which the pixel correspondence points plotted are converged as the degree of inflammation of the living tissue increases.

On the other hand, the closer to the healthy portion, the stronger the G component (or B component) of the color components of the image is with respect to the R component. Therefore, the boundary line between the area where the plots are distributed and the area where the plots are not distributed, which is the axis on the boundary line closer to the G axis than the R axis, that is, the axis on the boundary line passing through (0,0) and (255,192) in the example illustrated in FIG. 3 is set as an axis having a high correlation with the portion having a lowest degree of inflammation which is a portion considered to be a substantially healthy portion. This axis is the mucosal change axis AX2. The mucosal change axis AX2 is superimposed with plots corresponding to various imaging conditions, for example, the portion having the lowest degree of inflammation imaged under illumination light, that is, what is considered to be a substantially normal portion. Therefore, the mucosal change axis AX2 is the axis on which the pixel correspondence points plotted converge as the degree of inflammation decreases (closer to the healthy portion).

In addition, the highest degree of lesion in the lesion portion is accompanied by bleeding. On the other hand, the portion having the lowest degree of lesion is a substantially normal healthy portion, and is therefore covered with sufficient mucosa. Therefore, the plot in the RG color space illustrated in FIG. 3 can be regarded as being distributed in the region sandwiched between the axis most correlated with blood (hemoglobin pigment) and the axis most correlated with the color of the mucosa. Therefore, of the boundary lines between the areas where the plots are distributed and the areas where the plots are not distributed, the boundary line closer to the R axis (strong R component) corresponds to the axis indicating the inflamed portion having the highest degree of inflammation (hemoglobin change axis AX1), and the boundary line closer to the G axis (strong G component) corresponds to the axis indicating the inflamed portion having the lowest degree of inflammation (mucosal change axis AX2).

After setting the reference axis in this way, a process of calculating the living tissue redness, which indicates the intensity of red, which will be described later, is performed on the color component of the normally projected image. Before the process of calculating the living tissue redness, color correction is performed on the normally projected pixel data.

The reference axis illustrated in FIG. 3 is an example, and the reference axis varies depending on the type of disease.

The preprocessing unit 220a performs color correction on the color components of the image represented in the RG color space before calculating the inflammation evaluation value. The correction matrix coefficient is stored in the memory 204. The preprocessing unit 220a corrects the pixel data (R, G), which is the pixel correspondence point in the RG color space of each pixel, as illustrated in the following equation using the correction matrix coefficient so that the inflammation evaluation values described later do not vary (in other words, to suppress inter-individual error of the electronic scope) when images are taken with different electronic endoscope systems despite the same inflamed portion.

$$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

$R_{new}$: Corrected pixel data (R component)
$G_{new}$: Corrected pixel data (G component)
$M_{00}$ to $M_{11}$: Correction matrix coefficient
R: Pixel data before correction (R component)
G: Pixel data before correction (G component)

Figure 4:
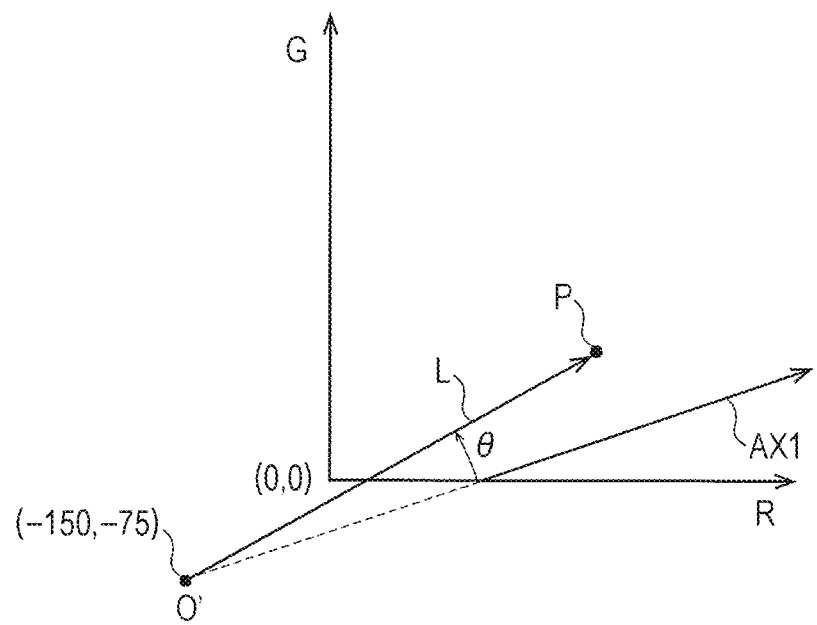
FIG. 4 is a diagram for explaining a method of calculating a deviation angle for calculating a living tissue redness used in one embodiment.

The image evaluation value calculation unit 220b selects one pixel of interest from the pixels, and calculates the deviation angle for calculating the degree of inflammation of the selected pixel of interest based on the information of the color component of the pixel of interest. That is, a quantification process is performed to quantify the degree of redness of the living tissue based on the information of the color component of the pixel. FIG. 4 is a diagram for explaining a method of calculating a deviation angle for calculating the living tissue redness used in one embodiment. Specifically, as illustrated in FIG. 4, the image evaluation value calculation unit 220b sets the intersection of the hemoglobin change axis AX1 and the mucosal change axis AX2 as a reference point O', and calculates the deviation angle θ at which the direction of the line segment L connecting the reference point O' and the pixel correspondence point P of the pixel of interest with respect to the hemoglobin change axis AX1. The reference point O' is located at the coordinates (−150, −75). The example in which the reference point O' is set to the coordinates (−150, −75) is given, but the invention is not limited to this. The reference point O' can be changed as appropriate, and may be, for example, the intersection of the R axis and the G axis in the RG color space.

A suitable coordinate position as the reference point O' is, for example, a position where an error in the evaluation result due to fluctuations in brightness can be reduced. Specifically, the reference point O' is preferably set by obtaining a point in advance where an error between the evaluation result in the dark portion (brightness is less than a predetermined value) and the evaluation result in the non-dark portion (brightness is more than a predetermined value) is minimized.

In addition, for example, if the reference point O' is set between the coordinates (−10, −10) and (10, 10), the coordinates (−150, −75) and the like are compared with the case where the reference point O' is set. Therefore, the amount of change in the angle θ when the pixel correspondence point changes becomes large, so that the resolution is improved. As a result, a highly accurate evaluation result can be obtained.

On the other hand, by setting the reference point O' between the coordinates (−50, −50) and (−200, −200), the evaluation result indicating the intensity of inflammation is not easily affected by noises.

When the brightness of an image of a living tissue inside an organ changes depending on the condition under the white light, the color of the image is generally affected by individual differences, the location of the image, the state of inflammation, etc. However, in the RG color space, the color of the image changes along the hemoglobin change axis AX1 in the inflamed portion where inflammation is most advanced, and changes along the mucosal change axis AX2 in the inflamed area where the degree of inflammation is the least. In addition, it is presumed that the color of the image of the inflamed portion where the degree of inflammation is intermediate changes with the same tendency. That is, the pixel correspondence point corresponding to the inflamed portion shifts in the azimuth angle direction starting from the reference point O' when the brightness of the pixel changes depending on the condition under the illumination light. In other words, when the brightness of the pixel changes depending on the condition under the illumination light, the pixel correspondence point corresponding to the inflamed portion moves while maintaining the deviation angle θ with respect to the hemoglobin change axis AX1 so that the distance from the reference point O' changes. This means that the deviation angle θ is a parameter that is substantially unaffected by changes in the brightness of the image.

The smaller the deviation angle θ, the stronger the R component with respect to the G component, indicating that the degree of redness in the lesion portion is relatively large. Further, the larger the deviation angle θ, the stronger the G component with respect to the R component, indicating that the degree of redness is relatively small. Therefore, the image evaluation value calculation unit 220b normalizes the angle θ so that the value becomes 255 when the deviation angle θ is zero and the value becomes zero when the deviation angle θ is $\theta_{MAX}$. Further, $\theta_{MAX}$ is equal to the angle formed by the hemoglobin change axis AX1 and the mucosal change axis AX2. That is, the evaluation value calculation unit 220b calculates the value in a range of 0 to 255, for each pixel of interest, which is obtained by normalizing the deviation angle θ calculated based on the information of the color component of the pixel of interest as the living tissue redness (pixel evaluation value).

The pixel of interest is selected one by one for all the pixels of the image.

In the example illustrated in FIG. 4, the RG color space is used as the color space, but the RB color space can be used instead of the RG color space.

The image evaluation value calculation unit 220b calculates the living tissue redness, which is a value obtained by normalizing the deviation angle θ, as the pixel evaluation value. In some cases, the whiteness of the living tissue indicating the intensity of characteristic of the ulcer of the living tissue can also be calculated as a pixel evaluation value. For example, the pixel value of each color component of each pixel of the image of the living tissue is adjusted to give a linear gain (gain), and tone enhancement processing for increasing the effective resolution of the color expression is performed by substantially widening a dynamic range near the color gamut peculiar to the lesion. For example, an ulcer part containing white moss and purulent mucus of ulcerative colitis can be distinguished from an inflamed portion and a healthy portion by the color component. The ulcer portion is white, while the inflamed portion including edema and bleeding is red, and the healthy portion is yellow or green. The whiteness of the living tissue can be calculated using a deviation angle with respect to the reference axis which is different from the hemoglobin change axis AX1, which is expressed on the color space having two color components (two of R component, G component, and B component) as illustrated in FIG. 4 or three color components (R component, G component, and B component) as the coordinate axes. The tone enhancement processing is performed by the preprocessing unit 220a.

The image evaluation value calculation unit 220b calculates one image evaluation value using the pixel evaluation value of each pixel, for example, the above-mentioned living tissue redness. This image evaluation value represents the intensity of lesion of the living tissue in the image, and the larger the value, the larger the intensity of lesion (the lesion is advanced). The image evaluation value calculation unit 220b may calculate, for example, the integrated value or the average value of the pixel evaluation values of all the pixels in the captured image as one image evaluation value, or may select pixels representing the image of the living tissue to be evaluated in the captured image and calculate the integrated value or the average value of the pixel evaluation values of the selected pixels as one image evaluation value. Alternatively, for example, among the RGB color component or pixel brightness component for each pixel, the pixels to be evaluated are extracted based on the color components or brightness components in a predetermined range, and the average value of the pixel evaluation values of the extracted pixels are obtained, or integration processing is performed, so that the image evaluation value calculation unit 220b may calculate one image evaluation value. The pixel portion to be evaluated in the image is a portion having a value of the color component within a predetermined range assumed in the living tissue in order to evaluate the degree of inflammation in an organ with high accuracy, and is preferably a portion of the pixel having a brightness component equal to or more than a predetermined value which is illuminated with an illumination light.

The image evaluation value calculated by the image evaluation value calculation unit 220b is sent to the lesion evaluation unit 220d.

The image evaluation value calculation unit 220b further creates a color map image in which the image of the living tissue is mosaicked with a display color that changes according to the living tissue redness. In order to create the color map image, a table in which the pixel evaluation value and the predetermined display color are associated with each other is stored in the storage area of the memory 204. In the above table, for example, different display colors are associated with each value in increments of 5. For example, blue is associated with a pixel evaluation value in a range of 0 to 5, and different display colors are associated according to the order of colors in the color wheel every time the pixel evaluation value increases by 5, and red is associated with the pixel evaluation value in a range of 250 to 255. The display color is a color that approaches a warm color from a cold color, for example, from blue to yellow to red as the living tissue redness increases. The image evaluation value calculation unit 220b determines the display color of the selected pixel of interest on the color map image based on the above table according to the living tissue redness of the pixel of interest.

In this way, the image evaluation value calculation unit 220b creates a color map image in which colors are added according to the pixel evaluation value.

The imaging position information processing unit 220c acquires the imaging position information sent from a position measurement system 250 provided in the electronic endoscope system 1, and associates the acquired information with the captured image. An example of the position measurement system 250 includes a system which acquires the position of the solid-state image sensor 108 located at the tip end portion of the electronic scope 100 inserted in the organ and each position of subsequent flexible tubes using sensors, a system which acquires the insertion length of the electronic scope 100 inserted from the open end of the organ, or a system which acquires a specific portion passing signal indicating that the tip end portion of the electronic scope 100 passes through a feature portion of the inserted organ by displaying the captured image in the monitor 300 and by a manual input of the operator who has viewed the image.

The acquired information of the imaging position is sequentially sent to the lesion evaluation unit 220d.

In the system that acquires the position of the solid-state image sensor 108 using a sensor, for example, a plurality of magnetic sensors are provided at positions near the solid-state image sensor 108 at the tip end portion of the electronic scope 100 and in the flexible tube following the tip end portion to the electronic endoscopy processor 200 side at predetermined intervals. The magnetic fields having different intensities depending on positions are applied from the outside of the human body to which the electronic scope 100 is inserted to the organ to measure the intensities of the magnetic fields by the magnetic sensor. Thereby, the position of the magnetic sensor provided at the tip end portion can be known, and the curved shape in the organ of the flexible tube can be known from the positions of the plurality of magnetic sensors. As a result, the position of the tip end portion of the solid-state image sensor 108 can be known, and the shape of the electronic scope 100 in the organ and the insertion length of the organ of the electronic scope 100 from the open end can be known.

In the case of a system that acquires the insertion length of the electronic scope 100 inserted from the open end of an organ, for example, the moving distance information regarding how much the living tissue has moved between adjacent frame images in the captured moving image is acquired using the processing of the optical flow, and the moving distance information is integrated as the frame image changes to calculate the moving distance, so that the information of the current insertion length of the electronic scope 100 can be acquired. Further, for example, the information of the current insertion length of the electronic scope 100 can be acquired by measuring the length of the flexible tube extending from the tip end portion of the inserted electronic scope 100 toward the inside of the organ.

In a system that acquires a signal passing through a specific part of an organ, while the operator sees the image displayed on the monitor 300, the operator presses the button at hand to generates a specific part passing signal at a time point when an identifiable specific part inside the organ appears in the image and passes through, and the imaging position information processing unit 220c can acquire this specific part passing signal. The positions of specific parts inside the organ are, for example, when the organ is the large intestine, a position where an ascending colon begins, a position where the ascending colon ends and the large intestine bends and a transverse colon begins, and a position where the transverse colon ends, the large intestine bends, and a descending colon starts, a position where the descending colon ends, the large intestine bends, and the sigmoid colon begins, a position where the sigmoid colon ends and the rectum begins, and a position where the rectum ends and reaches the anus.

The lesion evaluation unit 220d calculates a representative evaluation value of the image evaluation value from the image evaluation values of a plurality of images of the living tissue imaged in each of the plurality of sections for each section. The plurality of sections are sections in which the captured image of the area inside the organ is divided at predetermined intervals. Since the image of the living tissue is associated with the imaging position information in the imaging position processing acquisition unit 220c, it is possible to grasp a section of the image of the living tissue using this imaging position information. Further, the lesion evaluation unit 220*d* evaluates the extent of lesion that continuously spreads in the depth direction inside the organ by using the representative evaluation value. For example, in the case of ulcerative colitis in the large intestine, it can be evaluated that the lesion has spread from the rectum to the descending colon. In such an evaluation, the extent of lesion can be evaluated assuming that the region where the representative evaluation value exceeds a preset threshold is the lesion portion.

Here, the section may be predetermined by the operator, or the section may be divided by the specific part passing signal. When a section is defined by a specific part passing signal, the section is called a segment.

This segment is a part of one organ that is distinguishable from the other, for example, if the organ is the large intestine, the ascending colon segment, the transverse colon segment, the descending colon segment, the sigmoid colon segment, the rectum segment, and the like. Such segments are separated into sections by the specific part passing signals.

According to one embodiment, the representative evaluation value calculated by the lesion evaluation unit 220*d* from the image evaluation value is preferably a statistic of the image evaluation value (hereinafter, the image evaluation value will be referred to as an image evaluation value belonging to each section) of the image of the living tissue included in each section.

By imaging the living tissue while moving the electronic scope 100 inside the organ, it is possible to evaluate the extent of lesion that is continuously spreading in the depth direction inside the organ by obtaining the representative evaluation value for each section.

The statistic preferably includes an average value, a median value, a mode value, or a maximum value. According to one embodiment, it is more preferable to use the maximum value from the viewpoint that the intensity of lesion can be optimally illustrated in the statistic.

According to one embodiment, the lesion evaluation unit 220*d* is configured to evaluate the intensity of lesion, which is a factor in the degree of lesion in an organ, using a plurality of ranks. It is preferable that the lesion evaluation unit 220*d* determines one of the plurality of ranks based on the representative evaluation value and evaluates the intensity of lesion for each section. This makes it possible to accurately inform the operator of the extent and intensity of lesion that continuously spreads in the depth direction inside the organ.

Further, according to one embodiment, it is preferable that the lesion evaluation unit 220*d* determines the presence or absence of a lesion portion in which the lesion is continuously spread in the depth direction of the organ for each section based on the representative evaluation value. The region of the lesion portion is a region in which the representative evaluation value is larger than the preset threshold.

According to one embodiment, it is also possible that the lesion evaluation unit 220*d* determines the presence or absence of a lesion portion in which the lesion is continuously spread in the depth direction of the organ based on the image evaluation value. The region of the lesion portion is a region in which the image evaluation value is larger than the preset threshold. Since the image evaluation value is an evaluation value for each image, it may include a noise component. In this case, it is preferable to use the representative evaluation value for each section instead of the image evaluation value.

At this time, the lesion position calculation unit 220*e* obtains the start position and the end position of the lesion portion by obtaining the section in which the lesion is located among the above sections based on the position information of the captured image, and specifies the location of the lesion portion. In order to accurately obtain the start position and end position of the lesion portion, it is also preferable to obtain the position where the image evaluation value crosses a predetermined threshold by using the image evaluation value and the position information of the captured image. In this case, the lesion evaluation unit 220*d* compares each image evaluation value with the threshold to determine whether the image evaluation value crosses the threshold. This determination result is sent to the lesion position calculation unit 220*e*. At this time, the lesion evaluation unit 220*d* preferably calculates the length of the lesion portion from the information on the start position and the end position of the lesion portion obtained by the lesion position calculation unit 220*e*.

Therefore, according to one embodiment, it is preferable that the monitor 300 displays at least one of the start position, the end position, and the length of the lesion portion on a screen. This makes it easier for the operator to recognize the extent of lesion of the organ in the depth direction.

In addition, the lesion evaluation unit 220*d* obtains the total value of the representative evaluation values corresponding to the section sandwiched between the start position and the end position of the lesion portion in the section, and it is preferable to evaluate the degree of lesion in the organ by this total value. This makes it possible to simultaneously evaluate the extent of lesion of the organ in the depth direction and the intensity of lesion. In this case, for example, the total value can be set to one of a plurality of levels and the degree of lesion can be evaluated by the level.

When many sections are set by narrowing the interval between predetermined sections, the lesion evaluation unit 220*d* laterally displays position information (for example, the distance from the deepest part of the electronic scope to the open end) along the depth direction of each section. In the graph illustrated with the representative evaluation value on the vertical axis, the curve created by the representative evaluation value for each section may be uneven in the adjacent section. In this case, according to one embodiment, it is preferable that moving average processing or curve fitting processing using a function indicating a predetermined curve is performed using the position information and the representative evaluation value of the section to smoothen the curve of the representative evaluation value illustrated in the graph.

Figure 5:
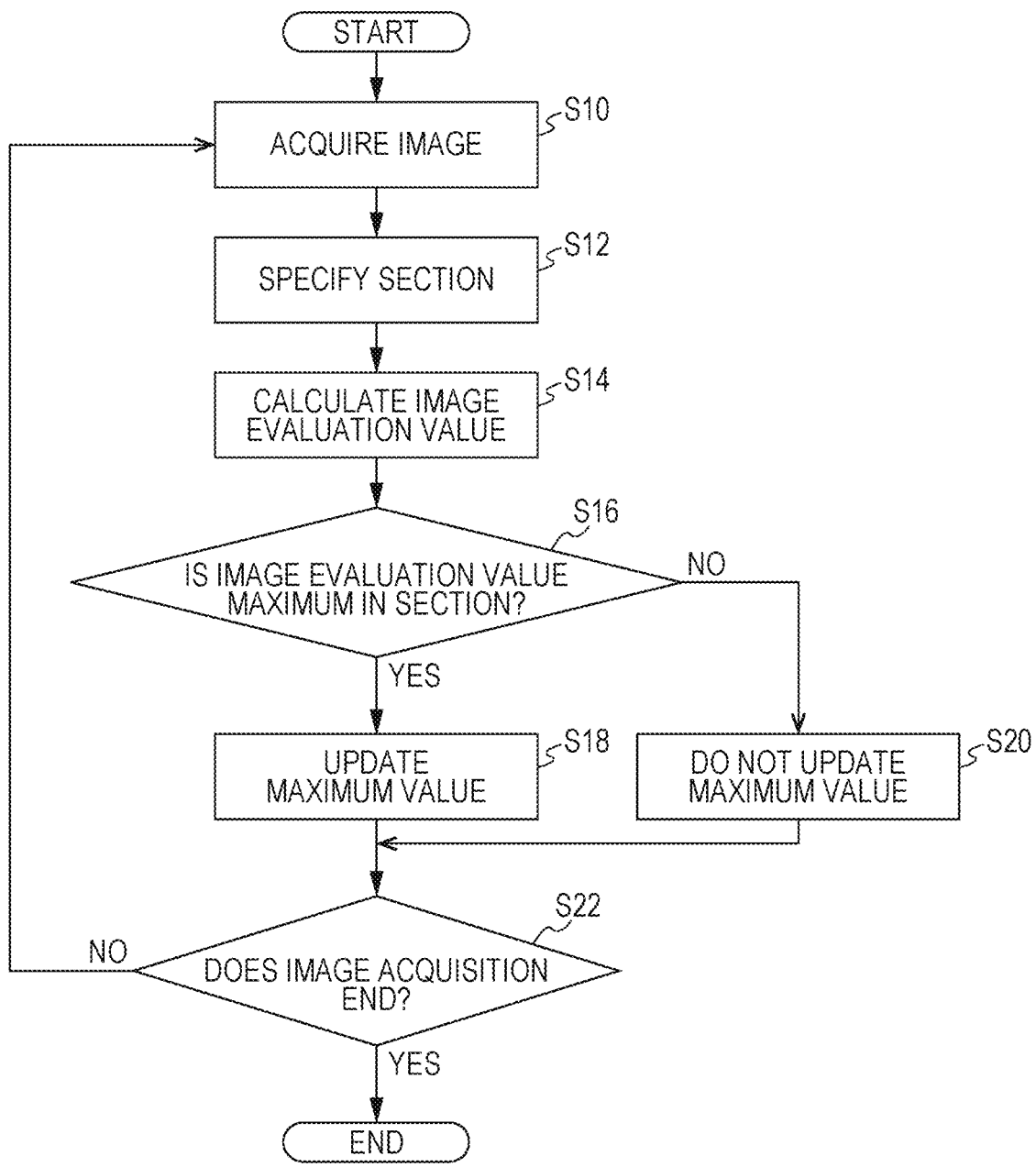
FIG. 5 is a diagram illustrating an example of a flow from image acquisition to obtaining a representative evaluation value for each section performed by an evaluation unit of one embodiment.

FIG. 5 is a diagram illustrating an example of a flow performed by the image processing unit 220 from image acquisition to obtaining a representative evaluation value for each section. In the example illustrated in FIG. 5, the maximum value among the image evaluation values corresponding to the section is used as the representative evaluation value.

First, the preprocessing unit 220*a* acquires an image (Step S10) and performs the above-described processing (RGB conversion, color space conversion, reference axis setting, color correction). At this time, the imaging position information processing unit 220*c* acquires the information of the imaging position of the image acquired from the position measurement system 250 in association with the position measurement system 250. As a result, the lesion evaluation unit 220*d* uses the information of the imaging position to specify the section in which the acquired image is captured inside the organ among the predetermined sections (Step S12). On the other hand, the image evaluation value calculation unit 220b calculates the image evaluation value using the image processed by the preprocessing unit 220a (Step S14).

Further, Step S14 is not limited to being performed after Step S12, and can be performed before or at the same time as Step S12.

The lesion evaluation unit 220d determines whether the calculated image evaluation value is the maximum within the specified section (Step S16). When the calculated image evaluation value is larger than any other image evaluation values in the specified section, that is, the maximum value, the maximum value which is the representative evaluation value is updated (Step S18). If the calculated image evaluation value is not the maximum within the specified section, the maximum value which is the representative evaluation value is not updated (Step S20). In this way, Steps S10 to S22 are repeated until the preprocessing unit 220a determines that the acquisition of the image is completed (Step S22). In this way, the image processing unit 220 obtains the maximum value of the image evaluation value for each section.

The evaluation result integration unit 220f integrates, as the evaluation result, a graph illustrating the numerical value of the representative evaluation value for each section and the distribution of the representative evaluation value in each section for the section, information indicating the extent of lesion portion in the depth direction, information of the start position, the end position of the lesion, or the length of the lesion portion, and information of the ranked intensity of the lesion portion for each section, and displays the evaluation result in the monitor 300 as one or a plurality of evaluation result screens.

Figure 6:
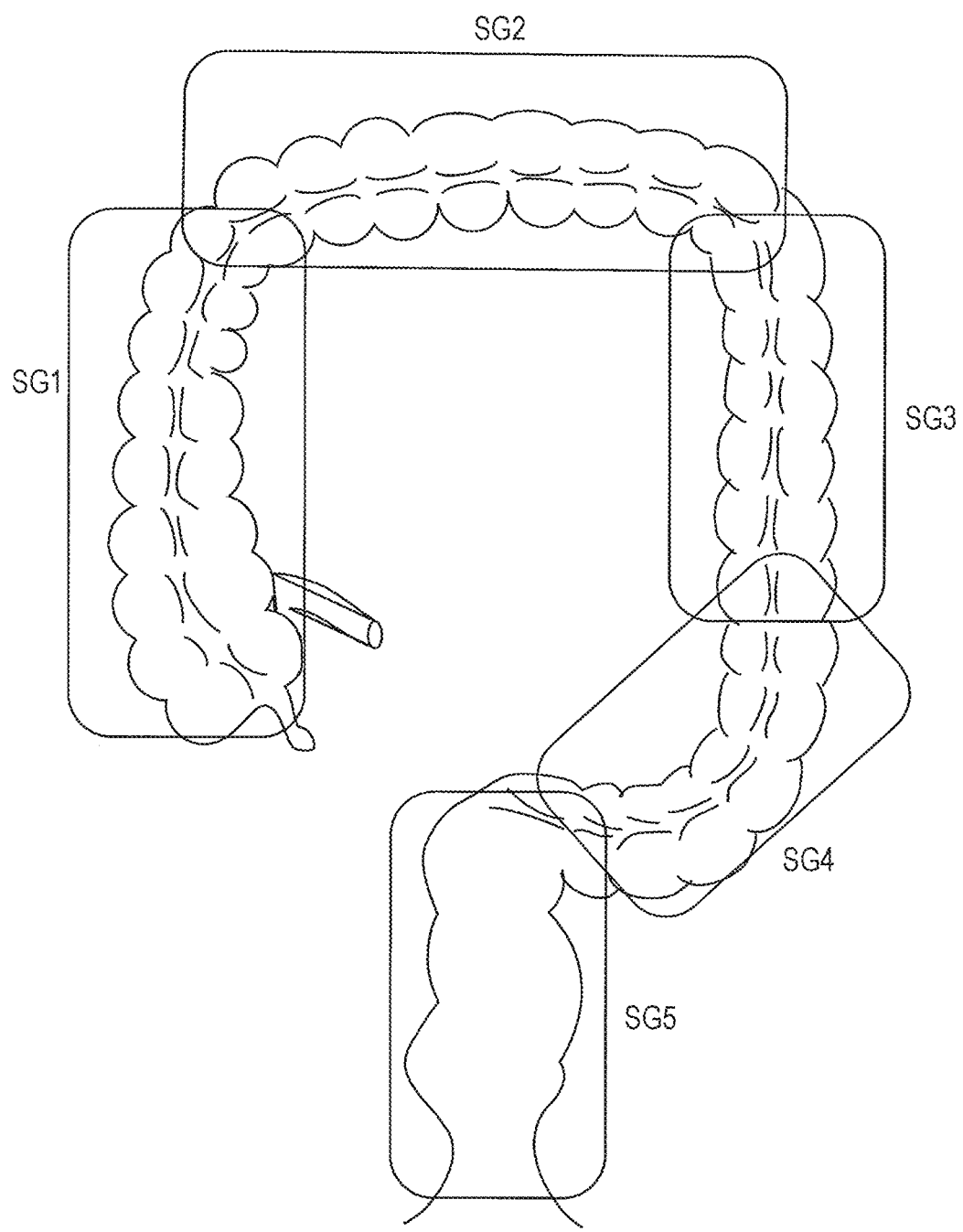
FIG. 6 is a diagram for explaining a large intestine, which is an example of an organ to be measured by the endoscope system of one embodiment.

FIG. 6 is a diagram for explaining a large intestine, which is an example of an organ. The large intestine includes the rectum, sigmoid colon, descending colon, transverse colon, and ascending colon, in order from the open end (anus). Hereinafter, the rectum is referred to as segment SG5, the sigmoid colon is referred to as segment SG4, the descending colon is referred to as segment SG3, the transverse colon is referred to as segment SG2, and the ascending colon is referred to as segment SG1.

Generally, the electronic scope 100 is inserted to the deepest part of segment SG1 which is the ascending colon, and moves from there so as to be pulled out toward the open end side at a substantially constant moving speed. Therefore, the electronic scope 100 captures images in the order of segment SG1, segment SG2, segment SG3, and so on.

Figure 7:
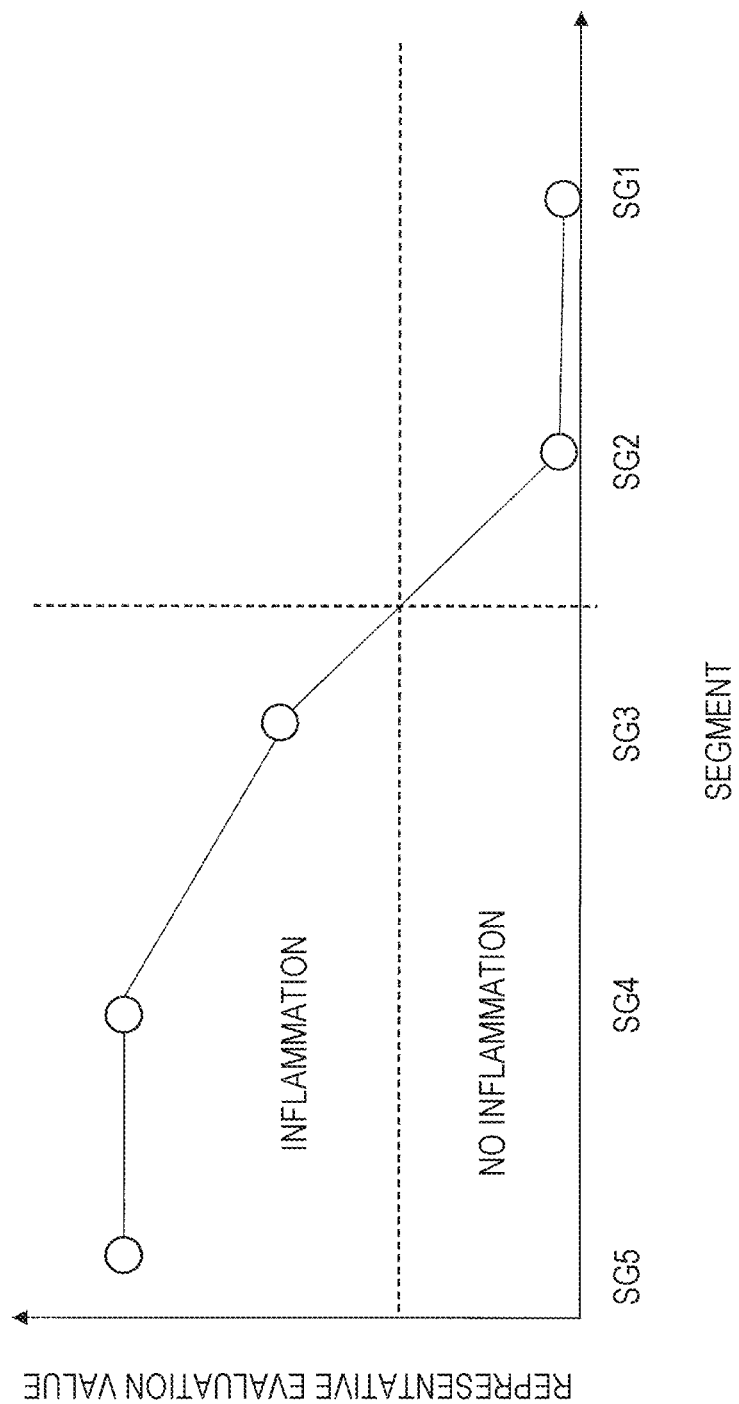
FIG. 7 is a diagram illustrating an example of an evaluation result by a lesion evaluation unit of one embodiment.

FIG. 7 is a diagram illustrating an example of the evaluation result by the lesion evaluation unit 220d. In the graph of FIG. 7 illustrating the evaluation result, the horizontal axis represents positions from segment SG5 to segment SG1, and the vertical axis represents the representative evaluation value. In FIG. 7, a plurality of sections are designated as segments SG1 to SG5, and segments having a representative evaluation value equal to or higher than the threshold are illustrated as inflamed lesion portions with a predetermined threshold as a boundary. The example illustrated in FIG. 7 shows that the entire segment SG5, the entire segment S4, and a part of segment SG3 are inflamed. According to one embodiment, such an evaluation result is displayed on the monitor 300. Further, according to one embodiment, the lesion evaluation unit 220d evaluates that the lesion portion extends from the middle of segment SG3 to segment SG5. The evaluation result is displayed on the screen of the monitor 300.

Figure 8:
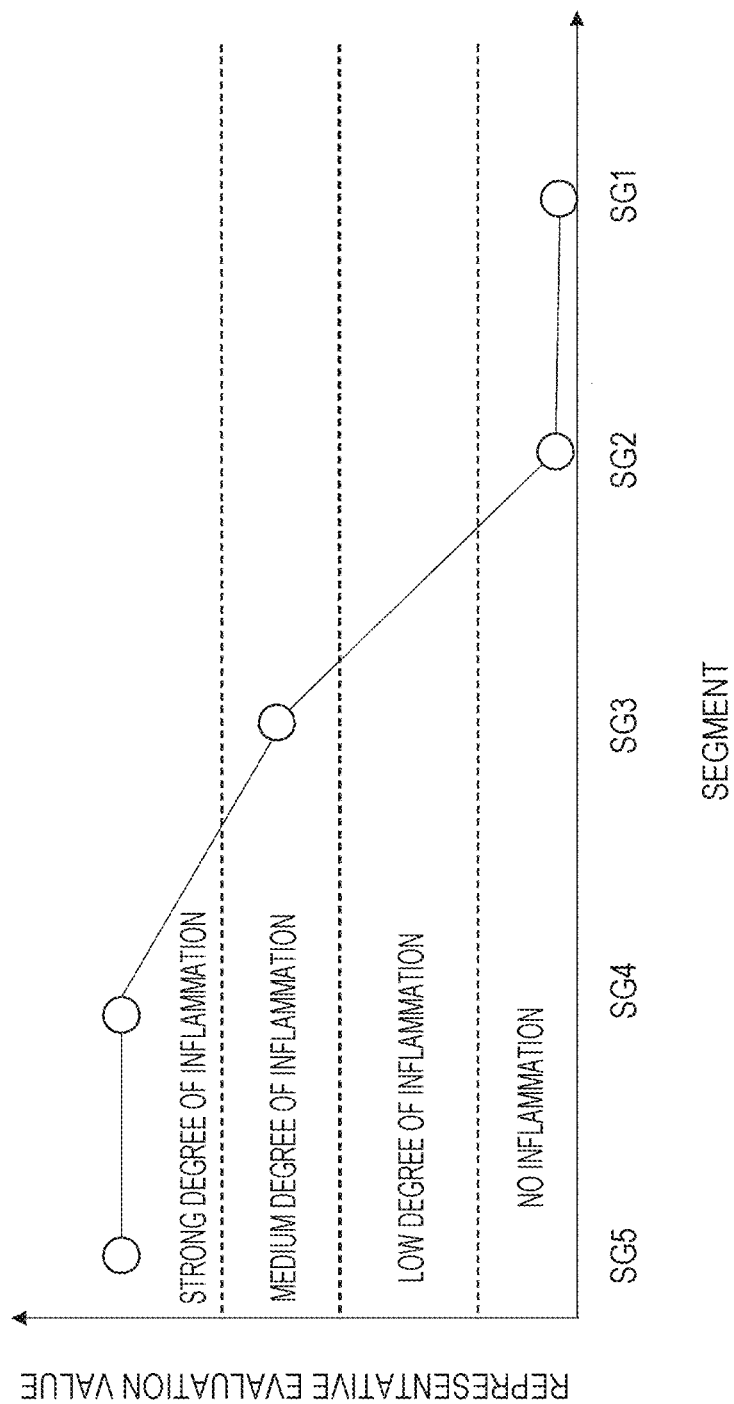
FIG. 8 is a diagram illustrating another example of the evaluation result by the lesion evaluation unit of one embodiment.

FIG. 8 is a diagram illustrating another example of the evaluation result by the lesion evaluation unit 220d. Similar to FIG. 7, in the graph of FIG. 8 illustrating the evaluation result, the horizontal axis represents positions from segment SG5 to segment SG1, and the vertical axis represents the representative evaluation value. In the example illustrated in FIG. 8, the evaluation of the intensity of lesion (inflammation) in each section is evaluated by a plurality of ranks regarding the intensity of lesion (inflammation), that is, one of five stages of "strong degree of inflammation", "medium degree of inflammation", and "low degree of inflammation", and "no inflammation". The lesion evaluation unit 220d determines one of the plurality of ranks for each segment based on the representative evaluation value, and evaluates the intensity of lesion (inflammation) for each segment. Therefore, in the example illustrated in FIG. 8, lesions (inflammation) exist from a part of segment SG3 to segment SG5, and the intensity of lesion (inflammation) in segment SG5 and segment SG4 is evaluated to be strong, and the intensity of lesion (inflammation) of segment SG3 is evaluated as an intermediate degree. According to one embodiment, such an evaluation result is displayed on the monitor 300.

Figure 9:
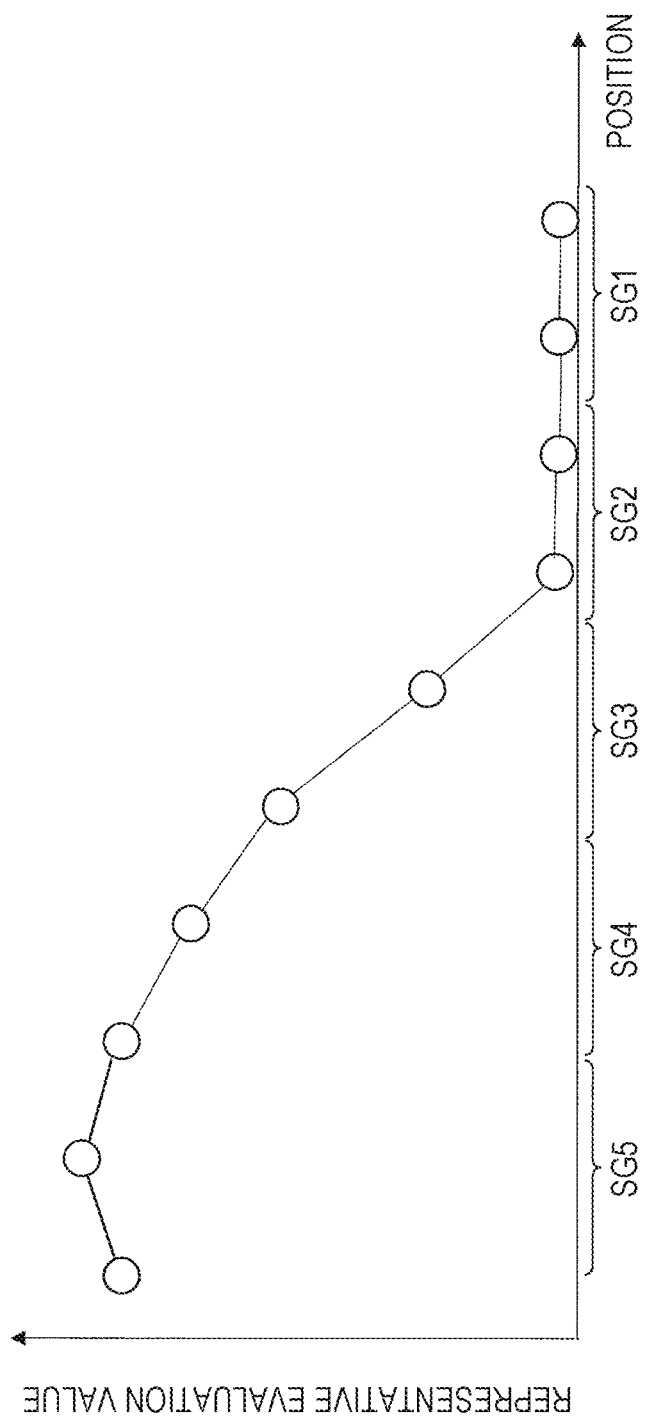
FIG. 9 is a diagram illustrating another example of the evaluation result by the lesion evaluation unit of one embodiment.

FIG. 9 is a diagram illustrating another example of the evaluation result by the lesion evaluation unit 220d. In the graph in FIG. 9 illustrating the evaluation result for each section, the horizontal axis represents the position in the large intestine in the depth direction, and the vertical axis represents the representative evaluation value. In FIG. 9, the sections show a narrower range than segments SG1 to SG5, and more specifically, the sections in which each segment is divided into two are set. Also in the example illustrated in FIG. 9, a section having a representative evaluation value equal to or higher than the threshold can be defined as an inflamed lesion portion with the predetermined threshold as a boundary. According to one embodiment, such an evaluation result is displayed on the monitor 300. Further, according to one embodiment, the lesion evaluation unit 220d evaluates that the lesion portion extends from a section of segment SG3 to the last section of segment SG5. The evaluation result is displayed on the screen of the monitor 300.

Figure 10:
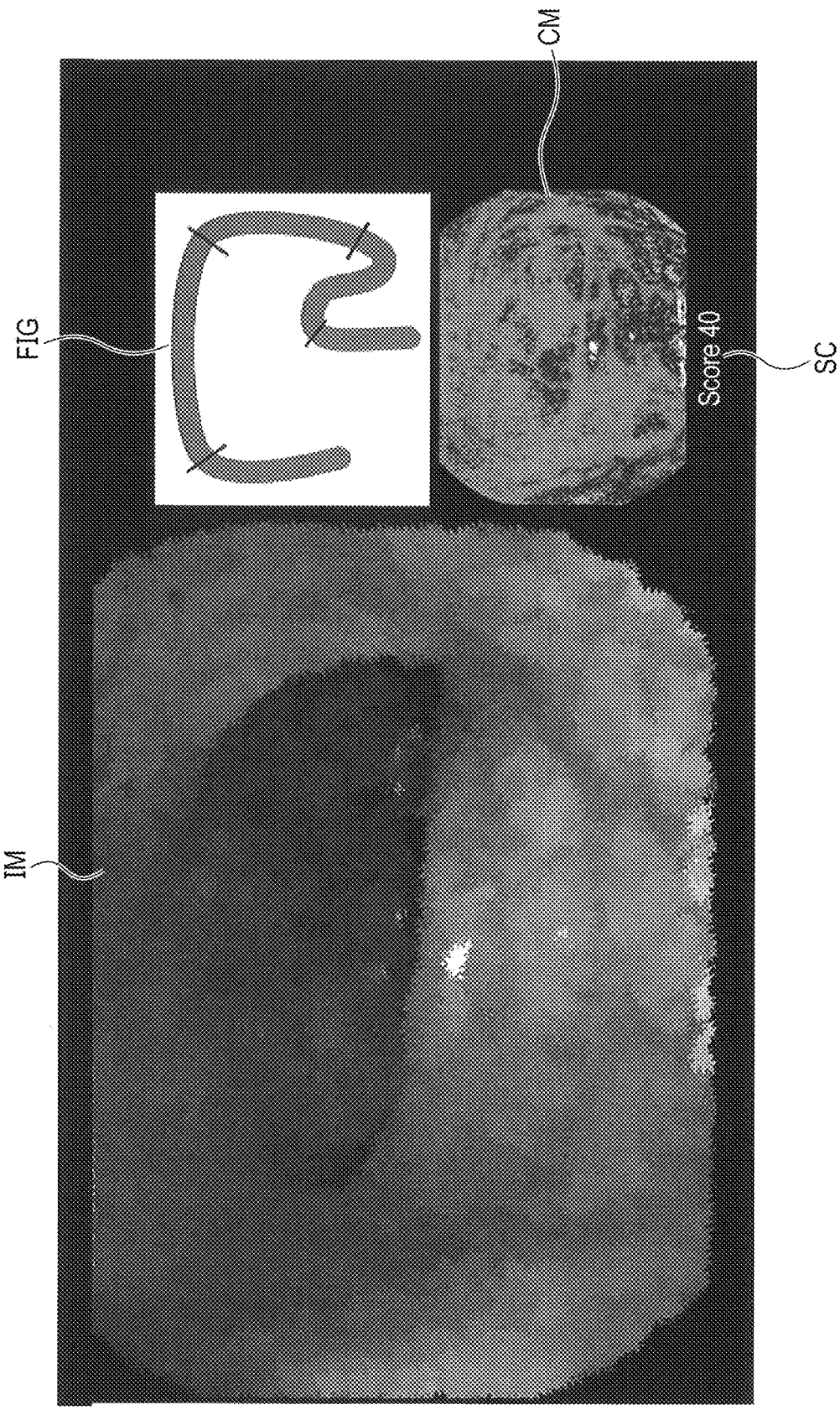
FIG. 10 is a diagram illustrating an example of a screen including one frame of a moving image displayed on a monitor of one embodiment.

FIG. 10 is a diagram illustrating an example of a screen including one frame of a moving image displayed on the monitor 300. In the example illustrated in FIG. 10, a captured image IM is illustrated on the left side of the screen. A large intestine schematic diagram Fig, which schematically illustrates the large intestine, is illustrated in the upper right of the screen. In the lower right of the screen, a color map image CM obtained by converting the color of each pixel of the image illustrated on the left side of the screen according to the pixel evaluation value indicating the intensity of inflammation is displayed. On the lower side, a score SC which is the image evaluation value indicating the intensity of inflammation is displayed. In the example illustrated in FIG. 10, the score SC is 40.

Figure 11A:
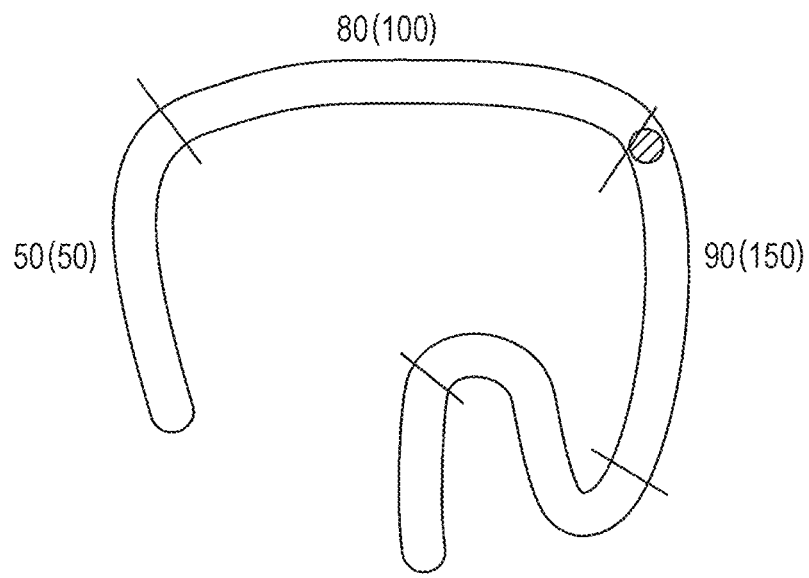
FIG. 11A is a diagram illustrating another example of a screen displayed on the monitor of one embodiment.
Figure 11B:
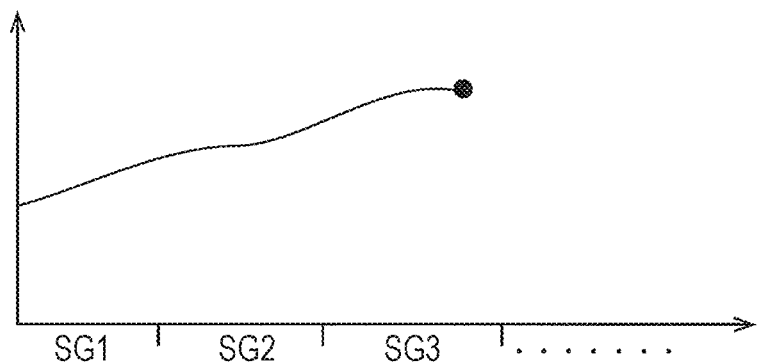
FIG. 11B is a diagram illustrating another example of a screen displayed on the monitor of one embodiment.
Figure 11C:
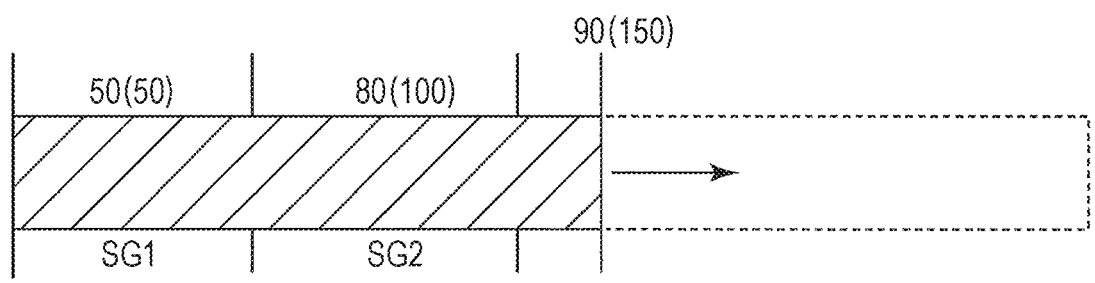
FIG. 11C is a diagram illustrating another example of a screen displayed on the monitor of one embodiment.

FIGS. 11A to 11C are diagrams illustrating another example of the screen displayed on the monitor 300.

FIG. 11A illustrates an example attached as an example of the evaluation result to the large intestine schematic diagram Fig illustrated in FIG. 10. In the large intestine schematic diagram Fig illustrated in FIG. 11A, the position information of the currently displayed image of the displayed image IM is indicated by a circle, and the representative evaluation value for each segment is illustrated. The representative evaluation value is 50 in segment SG1, the representative evaluation value is 80 in segment SG2, the representative evaluation value is 90 in segment SG3, and the representative evaluation value is currently being processed in segment SG4, and the tentative value is displayed to be 90. The representative evaluation value is displayed so that the display color of the representative evaluation value differs between the case where the representative evaluation value is currently being processed and the case where the representative evaluation value has been processed. Further, in FIG. 11A, the representative evaluation values evaluated by the electronic scope 100 most recently are illustrated in parentheses. This makes it possible to know which segment the intensity of lesion is lighter than the previous evaluation result and which segment the lesion strength is severer.

FIG. 11B illustrates another example of the screen display on the monitor 300. As illustrated in FIG. 11B, the horizontal axis represents the position of each segment, and the vertical axis represents the image evaluation value (for example, the living tissue redness). As illustrated in FIG. 10, when the image IM is continuously displayed as a moving image as illustrated in FIG. 10, the image evaluation value in the currently displayed image IM may be displayed in the graph as the representative evaluation value in accordance with timing of displaying the moving image. In this way, as the image IM is displayed as a moving image, the curve of the image evaluation value illustrated in FIG. 11B also extends.

FIG. 11C is a diagram illustrating another example of the screen display on the monitor 300. In the example illustrated in FIG. 11C, when the image IM is continuously displayed as a moving image as illustrated in FIG. 10, the position of the currently displayed image IM in the moving image data is illustrated by a bar graph, and the representative evaluation value for each segment in the image that has already been displayed is illustrated.

The various display screens displayed on the monitor 300 are integrated by the evaluation result integration unit 220*f* according to the input instruction of the operator, and a screen as illustrated in FIG. 10 is created.

The electronic endoscope system 1 described above may evaluate the extent of lesion in the depth direction of the organ online when the electronic scope 100 is currently inserted into the organ for measurement. The image and the information on the imaging position from the position measurement system 250 are recorded in the memory 204 in chronological order at the same timing, and at a later date, the extent of lesion in the depth direction of the organ may be evaluated while calculating the image evaluation value and the representative evaluation value while reproducing the image captured by the electronic scope 100.

When the evaluation is performed while reproducing the image captured by the electronic scope 100 and the information of the imaging position at a later date, the evaluation is not limited to the reproduction by the electronic endoscope 1.

For example, the image and the imaging position information recorded in the memory 204 are called from another data processing device, and the extent of lesion in the depth direction of the organ can be evaluated while calculating the image evaluation value and the representative evaluation value.

That is, the data processing device is a device with a monitor which evaluates the degree of lesion in the living tissue from a plurality of images of the living tissue in the tubular organ. This data processing device includes an image evaluation value calculation unit configured to calculate an image evaluation value indicating an intensity of lesion in a living tissue in each of a plurality of captured images of the living tissue inside the organ, an imaging position information processing unit configured to associate each image captured in the organ with acquisition information of an imaging position in the organ, a lesion evaluation unit configured to calculate a representative evaluation value of the image evaluation value from the image evaluation values of a plurality of images of the living tissue captured in each of a plurality of sections in which a captured image of a region in the organ is divided using the information of the imaging position, and to evaluate an extent of lesion which is continuously spreading in a depth direction of the organ using the representative evaluation value, and a monitor configured to display an evaluation result of the extent of lesion in a screen.

As described above, in the electronic endoscope system and the data processing device, the representative evaluation value of the image evaluation value is calculated from the image evaluation value for each of the plurality of sections, where the captured image of the region inside the organ is divided, using the information of the imaging position in the organ in which each image is captured. On the other hand, conventionally, the intensity of lesion is only evaluated for each image using the image evaluation value calculated for each image. Therefore, in the above-mentioned electronic endoscope system and the data processing device, the extent of lesion in the depth direction of the organ can be evaluated using the representative evaluation value, and the degree of lesion can be evaluated accurately using the extent of lesion and the intensity of lesion together.

Hitherto, the description has been given in detail about the electronic endoscope system and the data processing device of the invention. However, the electronic endoscope system and the data processing device of the invention are not limited to the above embodiments, and may of course be modified and altered in various ways with in a range not departing from the scope and spirit of the invention.

REFERENCE SIGNS LIST 1 electronic endoscope system
100 electronic scope
102 LCB
104 light distribution lens
106 objective lens
108 solid-state image sensor
108*a* IR cut filter
108*b* color filter
112 driver signal processing circuit
114 memory
200 electronic endoscopy processor
220 image processing unit
220*a* preprocessing unit
220*b* image evaluation value calculation unit
220*c* imaging position information processing unit
220*d* lesion evaluation unit
220*e* lesion position calculation unit
220*f* evaluation result integration unit
230 light source unit
300 monitor
400 printer
600 server

The invention claimed is:

1. An electronic endoscope system for evaluating the degree of severity of a lesion of a living tissue in an organ, comprising:
an electronic endoscope configured to image the living tissue in the organ;

a processor that includes an evaluation unit configured to process a plurality of captured images of the living tissue to evaluate the degree of severity of the lesion in the organ; and a monitor configured to display an evaluation result of evaluating the degree of severity of the lesion on a screen, wherein the evaluation unit includes an image evaluation value calculation unit configured to calculate an image evaluation value indicating the value of the intensity of a parameter of the lesion in each of the plurality of images of the living tissue in the organ, an imaging position information processing unit configured to associate each of the images with information of an imaging position in the organ in which each of the images is captured, and a lesion evaluation unit configured to calculate a representative evaluation value of the image evaluation values from the image evaluation values of the plurality of captured images of the living tissue in each of a plurality of sections in which a captured image of a region in the organ is divided using the information of the imaging position so as to evaluate the length the lesion which is continuously extends in a depth direction of the organ, wherein the lesion evaluation unit is configured to determine the presence or absence of a lesion portion in which the lesion continuously extends in the depth direction of the organ for each section based on the representative evaluation value, the evaluation unit includes a lesion position calculation unit which is configured to obtain a section where the lesion portion is located among the sections based on information of the imaging position so as to obtain a start position and an end position of a region of the lesion portion, the lesion evaluation unit is configured to calculate the length of the lesion portion from the start position and the end position of the lesion portion, and the monitor is configured to display at least one of the start position of the region of the lesion portion, the end position of the region of the lesion portion, and the length of the lesion portion on the screen.

2. The electronic endoscope system according to claim 1, wherein the lesion evaluation unit uses statistics of a plurality of the image evaluation values corresponding to captured images of the living tissue for each section as the representative evaluation values.

3. The electronic endoscope system according to claim 2, wherein the statistic is a maximum value of the plurality of the image evaluation values.

4. The electronic endoscope system according to claim 1, wherein the lesion evaluation unit is configured to evaluate the intensity of the parameter of the lesion, which is an element of the degree of severity of the lesion in the organ, using a plurality of ranks for each section, and wherein the lesion evaluation unit is configured to determine one of the plurality of ranks based on the representative evaluation value and evaluate the intensity of the parameter of the lesion for each section.

5. The electronic endoscope system according to claim 1, wherein the monitor is configured to display a graph illustrating a distribution of the lesions in the depth direction, in which a horizontal axis represents position coordinates indicating a position of the sections along the depth direction in the organ and a vertical axis represents the representative evaluation value.

6. An electronic endoscope system for evaluating the degree of severity of a lesion of a living tissue in an organ, comprising:

an electronic endoscope configured to image the living tissue in the organ;

a processor that includes an evaluation unit configured to process a plurality of captured images of the living tissue to evaluate the degree of severity of the lesion in the organ; and a monitor configured to display an evaluation result of evaluating the degree of severity of the lesion on a screen, wherein the evaluation unit includes an image evaluation value calculation unit configured to calculate an image evaluation value indicating the value of the intensity of a parameter of the lesion in each of the plurality of images of the living tissue in the organ, an imaging position information processing unit configured to associate each of the images with information of an imaging position in the organ in which each of the images is captured, and a lesion evaluation unit configured to calculate a representative evaluation value of the image evaluation values from the image evaluation values of the plurality of captured images of the living tissue in each of a plurality of sections in which a captured image of a region in the organ is divided using the information of the imaging position so as to evaluate the extent of the lesion which continuously extends in a depth direction of the organ, wherein the lesion evaluation unit is configured to determine the presence or absence of a lesion portion in which the lesion continuously extends in the depth direction of the organ for each of the sections based on the representative evaluation value thereof, the evaluation unit includes a lesion position calculation unit which is configured to obtain a section where the lesion portion is located among the sections based on information of the imaging position so as to obtain a start position and an end position of the lesion portion, and the lesion evaluation unit is configured to evaluate the degree of the severity of the lesion in the organ from a total value of the representative evaluation values corresponding to a section sandwiched between the start position and the end position of the lesion portion.

7. A data processing device with a monitor for evaluating a degree of severity of a lesion in an organ from a plurality of images of a living tissue in the organ, comprising:

an image evaluation value calculation unit configured to calculate an image evaluation value indicating the value of the intensity of a parameter of the lesion of the living tissue in each of the plurality of captured images of the living tissue inside the organ;

an imaging position information processing unit configured to associate each of the images with information of an imaging position in the organ in which each of the images is captured;

a lesion evaluation unit configured to calculate a representative evaluation value of the image evaluation values of the plurality of captured images of the living tissue for each of a plurality of sections in which a captured image of a region in the organ is divided using the information of the imaging position so as to evaluate the length of the lesion which is continuously extends in a depth direction of the organ; and a monitor configured to display an evaluation result of evaluating the extent of lesion on a screen, wherein the lesion evaluation unit is configured to determine the presence or absence of a lesion portion in which the lesion continuously extends in the depth direction of the organ for each section based on the representative evaluation value, the evaluation unit includes a lesion position calculation unit which is configured to obtain a section where the lesion portion is located among the sections based on information of the imaging position so as to obtain a start position and an end position of a region of the lesion portion, the lesion evaluation unit is configured to calculate the length of the lesion portion from the start position and the end position of the lesion portion, and the monitor is configured to display at least one of the start position of the region of the lesion portion, the end position of the region of the lesion portion, and the length of the lesion portion on the screen.

8. A data processing device with a monitor for evaluating the degree of severity of a lesion in an organ from a plurality of images of a living tissue in the organ, comprising:

an image evaluation value calculation unit configured to calculate an image evaluation value indicating the value of the intensity of a parameter of the lesion of the living tissue in each of the plurality of captured images of the living tissue inside the organ;

an imaging position information processing unit configured to associate each of the images with information of an imaging position in the organ in which each of the images is captured;

a lesion evaluation unit configured to calculate a representative evaluation value of the image evaluation values of the plurality of captured images of the living tissue for each of a plurality of sections in which a captured image of a region in the organ is divided using the information of the imaging position so as to evaluate the extent of the lesion which continuously extends in a depth direction of the organ; and a monitor configured to display an evaluation result of evaluating the extent of lesion on a screen, wherein the lesion evaluation unit is configured to determine the presence or absence of a lesion portion in which the lesion continuously extends in the depth direction of the organ for each of the sections based on the representative evaluation value thereof, the evaluation unit includes a lesion position calculation unit which is configured to obtain a section where the lesion portion is located among the sections based on information of the imaging position so as to obtain a start position and an end position of the lesion portion, and the lesion evaluation unit is configured to evaluate the degree of the severity of the lesion in the organ from a total value of the representative evaluation values corresponding to a section sandwiched between the start position and the end position of the lesion portion.

* * * * *